United States Patent [19]

Shimoni

[11] Patent Number: 4,580,054

[45] Date of Patent: Apr. 1, 1986

[54] METHOD AND APPARATUS FOR LOCATING A POINT IN A THREE-DIMENSIONAL BODY USING IMAGES OF THE BODY FROM A PLURALITY OF ANGULAR POSITIONS

[75] Inventor: Yair Shimoni, Jerusalem, Israel

[73] Assignee: Elscint, Inc., Boston, Mass.

[21] Appl. No.: 593,501

[22] Filed: Mar. 26, 1984

[51] Int. Cl.[4] ............................................. G01T 1/20
[52] U.S. Cl. ................................. 250/363 S; 250/369
[58] Field of Search ................. 250/363.1, 363.2, 363; 340/709; 364/414, 415

[56] References Cited

U.S. PATENT DOCUMENTS

| | | | |
|---|---|---|---|
| 4,095,107 | 6/1978 | Genna et al. | 250/363 SB |
| 4,259,725 | 3/1981 | Andrews et al. | 364/414 |
| 4,302,675 | 11/1981 | Wake et al. | 250/363 SB |
| 4,415,807 | 11/1983 | Friauf et al. | 250/363 SA |

*Primary Examiner*—Janice A. Howell
*Attorney, Agent, or Firm*—Sandler & Greenblum

[57] ABSTRACT

A set of two-dimensional views of a body are provided from successive azimuthal angles with respect to a given axis. The set of views of the body are successively displayed on a display screen which shows the body as rotating about an axis. A point of interest in the body also appears to rotate about the axis. That view at which the point of interest is maximally displaced from the apparent axis of rotation is used to determine the angular position of the point of interest. The true displacement of the point of interest from the axis of rotation and its true displacement along the axis of rotation are available from that view. Thus, the cylindrical coordinates of the point of interest are known. To check the accuracy with which the coordinates of the point of interest have been determined, a cursor is established in the stopped view, and the projection of the cursor in the other views is calculated in a conventional manner. While sequential display of the views continues, the cursor appears to move with but not relative to the point of interest if the cursor actually overlies the point of interest. If the cursor appears to move relative to the point of interest, the cursor is modified until no relative motion appears.

30 Claims, 6 Drawing Figures

METHOD AND APPARATUS FOR LOCATING A POINT IN A THREE-DIMENSIONAL BODY USING IMAGES OF THE BODY FROM A PLURALITY OF ANGULAR POSITIONS

TECHNICAL FIELD OF THE INVENTION

The present invention relates to a method of and apparatus for locating a point in a three-dimensional body using images of the body from a plurality of angular positions.

BACKGROUND OF THE INVENTION

Conventional x-ray imaging techniques produce a shadow view of a body under examination. However, such a view does not contain sufficient information to specify the depth of a given point of interest in the body. Further, it is often impossible to distinguish small objects because they are obscured by the structure of larger overlying radio-opaque, objects, e.g., bones. These drawbacks have led to the development of body-section radiography systems known as x-ray tomography.

Conventional radiographic transverse tomography seeks to view planar sections or slices which are perpendicular to the axis of a patient. In such systems, a radiation source and associated detector means are rotated in a plane about a body under examination for measuring the absorption of the body at each of a plurality of angular positions. Using one of a number of well-known reconstruction algorithms on the data obtained by scanning the patient, a two-dimensional distribution of absorption coefficients is calculated for a slice defined by the plane within which the source and detectors are rotated.

The above-described x-ray imaging techniques require transmission of ionizing radiation through the body under examination. In order to minimize radiation dose to a patient, alternative imaging systems which reduce radiation exposure are employed in certain applications. Single-photon emission computerized tomography (ECT) is such an alternative imaging system. In carrying out an ECT session, the patient is first injected with a substance which, in itself, is innocuous, such as one of the natural substances of the body, and which is labeled with a radioactive tracer, or radioisotope. This tracer preferably has a short half-life so that very little radiation remains in the body after the examination has been completed. The tracer preferably emits gamma rays which are not readily absorbed by the body so that an appreciable part of the radiation will escape the body rather than be absorbed by it. The emission is preferably at a single energy so that detection can be made more easily and so that more accurate knowledge about the absorption factor of the body tissue through which the gamma ray has passed can be obtained.

Next, a gamma camera is used to scan the patient by moving the gamma camera around the patient in a closed, usually circular trajectory. The circular trajectory, e.g., enables the camera to obtain a series of measurements where each elemental area of the detecting surface of the camera traces a circular trajectory while the detecting surface is maintained perpendicular to the radius at all times, the radius being defined as the radius vector from the axis of rotation to the center of the camera. The simplest such rotation is of course one in which the axis of rotation coincides with the chosen axis of the coordinate system.

Emission data thus obtained while the camera is located at a particular predetermined angular position with respect to the axis of rotation, constitute a two-dimensional image that represents a view of the patient at the predetermined angular position. Such data are stored in what is termed herein, a memory frame. If a memory frame is obtained for each 3° of rotation of the gamma camera, 120 such frames will be obtained by a complete circuit of the patient by the camera.

Related lines in each memory frame so obtained constitute data associated with a single plane perpendicular to the axis of rotation of the camera about the patient. The data in such lines thus are analogous to views that would be obtained were transmission scanning of the patient carried out in such plane. By processing the data contained in the memory frames using a reconstruction algorithm similar to that used in transmission tomography, one obtains images of transverse sections through the patient at many different axial locations along the axis of rotation. Because of the nature of the ECT technique itself and also assumptions made with regard to the reconstruction algorithm, the cross-sectional images obtained are of relatively poor quality. Consequently, while using the ECT technique to obtain data reduces the radiation dose to a patient as compared to using transmission tomography, reconstructed cross-sectional images produced from the data so-obtained do not permit an interpreter of such images to precisely locate a point of interest in the patient, and do not enable the interpreter to estimate the density of the radioactive matter at that point quantitatively.

It is therefore an object of the present invention to improve the precision with which a point of interest in a patient can be located employing data obtained using the above-described ECT or similar techniques.

SUMMARY OF THE INVENTION

According to the present invention, a point of interest in a body is located by sequentially and repetitively displaying a set of two-dimensional views of the body at successively different angular positions with respect to a central axis of rotation, selecting a point in the body by establishing a cursor in each set of views corresponding to the selected point whereby the spatial location of the selected point relative to a reference coordinate system is determined, and moving the cursor until the selected point is coextensive with the point of interest. In determining whether this situation obtains, the views are sequentially displayed: if the cursor appears to an observer to move with the point of interest but not relative to the point of interest from view-to-view, then the selected point coincides with the point of interest.

The two-dimensional views of the body are established by the various memory frames containing data obtained during the circular circuit of the body by a gamma camera. When these views are sequentially displayed, the body appears to the viewer as a three-dimensional object rotating about an axis colinear with the axis about which the gamma camera rotates. A cursor is set into the display and positioned at a particular location, for example by moving it with a joystick to coincide with a particular location, i.e., a point of interest. The processor calculates the projected location of the cursor in each view and makes an appropriate entry into each memory frame. This establishes the spatial location of an operator-selected point in the body as the views are sequentially displayed. Only if the cursor appears to an observer to move with a point of interest in the body but not relative thereto will the cursor coincide with the point of interest. Because the cursor is computer generated, the coordinates of the point of interest with reference to the apparent axis of rotation of the body or to some other coordinate system will be known. With this information, the actual location of the point of interest in the body is determined. This information is useful directly by a physician or indirectly by identifying the reconstructed cross-section containing the point of interest and its location within the cross-section.

Preferably, the cursor is aligned with the point of interest while the display is moving as hereinbefore described. However, in an alternative technique for locating the cursor, the observer of the display stops the rotation of the body at that frame in which the point of interest reaches its maximum displacement from the apparent axis of rotation of the body. The display is conveniently stopped by "freezing" the display at the selected view. The exact frame at which maximum displacement occurs may be identified by a back-and-forth scrolling of the frames; but identification of the frame establishes the azimuth ($\theta_0$) of the gamma camera at which the plane of the detector head of the camera is parallel to a plane containing the point of interest and passing through the axis of rotation of the camera. This being the case, the actual distance of the point of interest from the axis of rotation $r_0$ and the elevation of the point of interest measured along the axis of rotation $Z_0$ can be measured. In a known manner, a cursor can be established in the identified frame so as to overlie the point of interest thereby establishing the cylindrical coordinates $r_0$, $Z_0$, $\theta_0$, of the point of interest. The projection of the cursor in each of the other frames can be calculated in a known manner so that, in the technique which includes stopping the display, when the frames are again sequentially displayed when rotation of the body resumes, the cursor appears to rotate with the body, or, in the technique which includes aligning the cursor with the point of interest while the display is moving, the cursor appears to rotate with the body as the frames continue to be sequentially presented to display the rotating body. If the cursor appears to coincide with the point of interest through the entire rotation of the body, then a conclusion is reached that the cursor overlies the point of interest. Any relative movement between the cursor and the point of interest indicates a lack of congruence requiring the operator to more carefully establish the position of the cursor.

Preferably, the cursor position is established via a manual input by the operator (e.g., by joystick and keyboard input). A computer associated with the system automatically computes the projection of the cursor in each frame for showing the cursor in each frame. Thus, the operator selected position is displayed in every view as the latter appears in the display. If the cursor appears to coincide with the point of interest during the entire rotation of the body, the cursor can be considered as overlying the point of interest. The readout of the cursor position provides spatial location of the point of interest.

The present invention also provides a method of non-reconstructively determining the three-dimensional position of a point of interest in a body as follows. A set of two-dimensional views of the body from successive angular increments about a given axis is generated by measuring the amount of radiation emitted by the body after injecting the body with a substance labelled with a radioactive tracer. The two-dimensional views so generated are successively displayed on a display means, and the three-dimensional coordinates associated with the location of the point of interest within the body are established. The projected location of the point of interest in each view in the set of two-dimensional views is calculated, and the projected location for each view is displayed as each view is displayed on the display means.

The present invention further provides a method of determining the position of a point of interest in a body as follows. A set of two-dimensional views of the body from successive angular increments about a given axis are generated, and the two-dimensional view within this set which is closest to the point of interest is determined. The closest two-dimensional view is then marked at a point which is closest to the point of interest, and the two-dimensional view with this marking is displayed. The two-dimensional view which is closest to the point of interest can be determined by successively displaying the two-dimensional views on a display means and stopping the display means at a particular angular view at which the point of interest is approximately at a maximum distance from an apparent axis of rotation of the two-dimensional views being successively displayed on the display means. Alternatively, the closest two-dimensional view can be marked at a point which is closest to the point of interest by moving a position indicating means associated with the display means to superimpose the position indicating means over the displayed point of interest while the two-dimensional views are being successively displayed on the display means, and simultaneously with moving the position indicating means, calculating and displaying the projected location for said position indicating means in each view in the set of two-dimensional views such that for each point to which the position indicating means is moved, the position indicating means appears to rotate about the apparent axis of rotation of the two-dimensional views on the display means in synchronism with the apparent rotation of the two-dimensional views.

BRIEF DESCRIPTION OF THE DRAWINGS

Embodiments of the present invention are shown by way of example in the accompanying drawings, wherein.

DETAILED DESCRIPTION OF THE INVENTION

Figure 1:
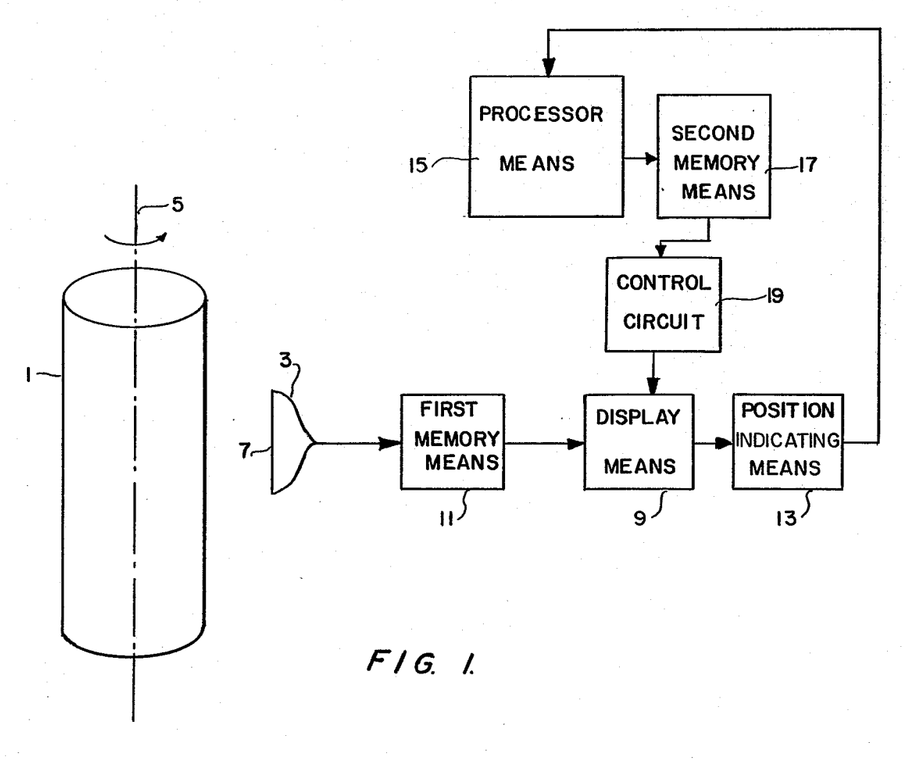
FIG. 1 is a block diagram of an apparatus according to the present invention for non-reconstructively determining the three-dimensional position of a point of interest in a body.

Referring now to FIG. 1, reference numeral 1 illustrates a body to be examined using imaging means 3, which is illustrated as a gamma camera. Where imaging means 3 is a gamma camera, it is used to generate a set of two-dimensional views of body 1 at successive angular increments about axis 5. These views can be obtained either by rotating object 1 about axis 5 while keeping imaging means 3 stationary, or by moving means 3 around body 1 in a closed trajectory, usually circular, with respect to axis 5. In either case, imaging means 3, which preferably has a flat two-dimensional surface 7 facing body 1, is enabled to obtain a series of two-dimensional views of body 1, where each pixel or elemental area of the flat surface 7 of imaging means 3 facing body 1 traces a circular trajectory while keeping surface 7 pointing perpendicularly at all times to a radius vector from a axis of motion 5 to imaging means 3. The radius vector is defined as a vector which is perpendicular to the axis of motion and which points toward the camera. The axis of motion 5 may be local; it may be changed periodically during the rotation in any desired predetermined or operator-controlled manner.

It should be noted that where imaging means 3 is an x-ray device, a set of two dimensional views of body 1 at successive angular increments is produced, whereas if imaging means 3 is a transmission CT device, a set of one-dimensional views of body 1 at successive angular increments is produced. Where such one-dimensional views of a planar slice of the body are produced, the apparatus and method of the present invention enable the two-dimensional position of a point of interest in a planar slice of the body to be determined.

In the following, the invention is described by reference to the use of a gamma camera as imaging means 3, and it should be understood that the principles of the invention equally apply to other types of imaging means as well.

Referring still to FIG. 1, where imaging means 3 is a gamma camera, means 3 includes detection means for measuring the amount of radiation emitted by body 1 after the body has been injected with a substance, preferably a substance natural to the body and labeled with a radioactive tracer, i.e., a radioisotope. Other emission CT techniques for using a gamma camera to generate a set of two-dimensional views of a body can be used, the present invention not being limited in scope to the above-described emission CT technique.

Display means 9 receives data representing the above-described set of two-dimensional views and is used to successively display these two-dimensional views. The human eye-brain combination can very easily give three-dimensional interpretation to these changing two-dimensional images on the display, so that the displayed image appears to rotate about an axis which corresponds to the actual axis 5 about which body 1 or imaging means 3 is moved. Display means 9 can be, for example, a cinematic screen associated with a cine camera.

First memory means 11 can be used to store data provided by imaging means 3. This data is then provided, when desired, to display means 9.

Display means 9 includes position indicating means 13 which is capable of selectively marking a pixel or elemental area on the display screen of display 9. Means 13 can be a cursor movable to any position on the display screen. Data representing the position of means 13 is fed to processor 15 which calculates the projected location of this position for each view in the set of two-dimensional views of the body provided by imaging means 3. Control circuit 19 receives data representing these projected locations from processor 15 and cooperates with display 9 to display the projected locations of the marked pixel or elemental area for each view in the set of two-dimensional views simultaneously with the successive display of the two-dimensional views on display 9 so that the marked pixel appears to rotate in syncronism with the successively-displayed two-dimensional views on the display screen.

Second memory means 17 can be used to buffer the output from processor 15 before it is sent to display circuit 19.

Figure 2A:
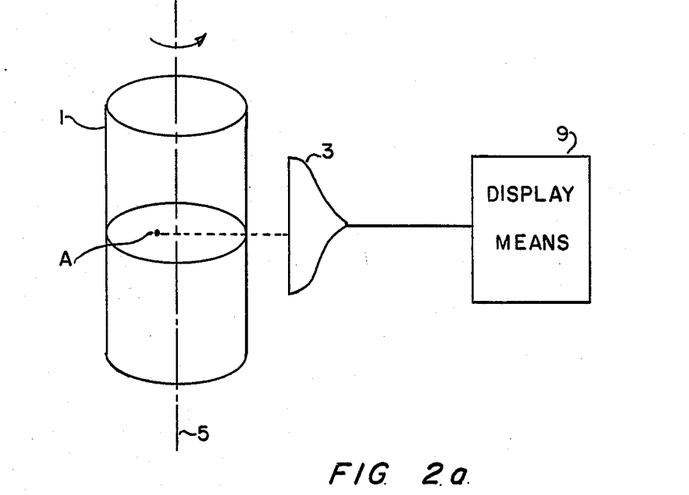
FIG. 2a illustrates a body under examination with a point of interest marked in a section thereof, along with imaging means.
Figure 2B:
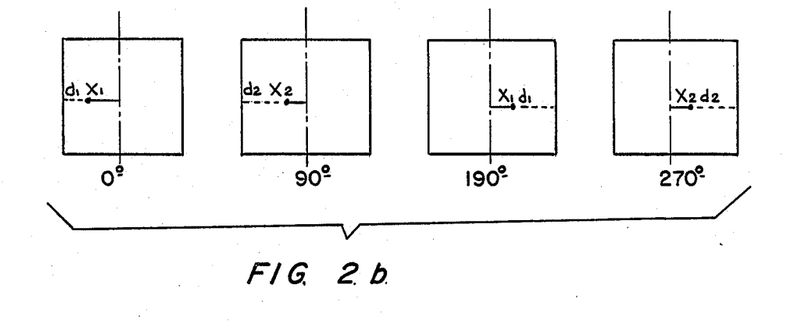
FIG. 2b illustrates views of the point of interest from successive angles approximately 90° apart from one another.

The method of the present invention provides for non-reconstructively determining the position of a point of interest in a body under examination. As illustrated in FIG. 2, such method includes generating a set of two-dimensional views of a body 1 using imaging means 3, e.g., a gamma camera, from successive angular increments with respect to an axis of motion 5. This set of two-dimensional views can be generated as described above either by rotating body 1 about axis 5 while maintaining imaging means 3 in a fixed position, or by moving means 3 about body 1. Also as discussed above, imaging means 3 can be an x-ray device producing two-dimensional views or a conventional transmission CT device producing a set of one-dimensional views of a planar slice of the body.

The method of the present invention will be further described below with respect to a gamma camera, but it should be understood that the description equally applies, with appropriate modifications, to both an x-ray device or a transmission CT device.

Figure 3:
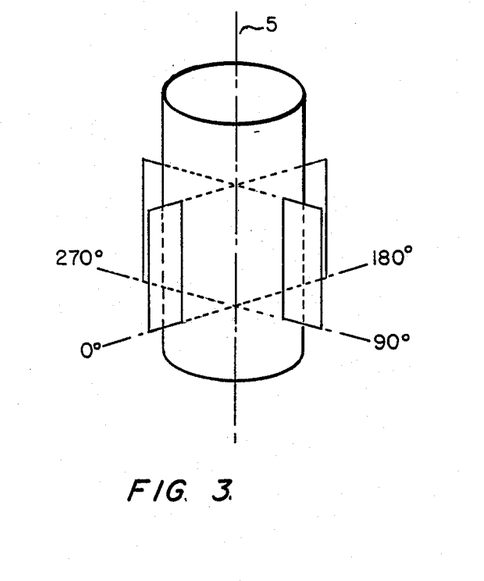
FIG. 3 illustrates the angular relationship between the angular views shown in FIG. 2b.
Figure 4:
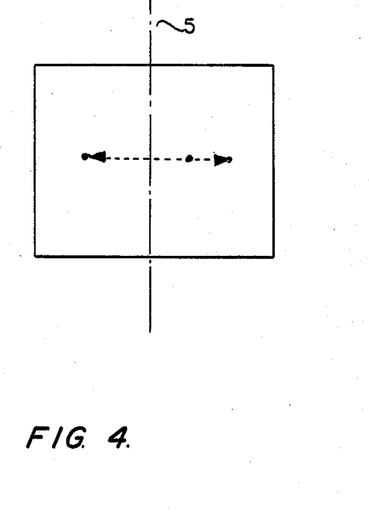
FIG. 4 illustrates movement of the point of interest on a display screen when the four frames of FIG. 2b are displayed on the screen in succession.

In FIG. 2a, reference symbol "A" represents a point of interest within body 1. FIG. 2b shows point "A" from four different angular views 90° apart from one another. FIG. 3 illustrates the angular relationship between the four views shown in FIG. 2b. FIG. 4 illustrates the movement of point "A" on the screen of display 9 when the four frames of FIG. 2b are displayed thereon in succession.

Where display means 9 is cinematic means including a cine camera, the display provides for cinematically varying two-dimensional images. As the successive frames are displayed, in most cases, the point of interest will appear to move on the screen because it is being seen from varying angles. The sole exception to this movement occurs when the point of interest is located on the axis of motion of imaging means 3 or the axis of rotation of body 1. Each point within the displayed image which is at a particular height above a chosen zero height will appear to move only along a line at that particular height in the case where perpendicular, parallel-hole collimators are used with a gamma camera. This same effect is achieved in a conventional transmission CT device in which the source means and the detector means are located in a common plane. Moreover, with respect to conventional x-ray devices, this same effect likewise is easily achievable.

According to one aspect of the method of the present invention, the cursor is superimposed over the point of interest while the display is moving, and the processor simultaneously calculates and displays the projected location for the cursor in each view such that for each point to which the cursor is moved, it appears to rotate in synchronism with the body. On-line calculation of the projected location through noting the angle or time when the point of interest appears farthest from the apparent axis of rotation provides accurate results, and angles can be calculated for which no actual image exists, i.e., by an interpolation between the successive, spaced angular views.

According to another aspect of the method of the present invention, display means 9 is stopped or frozen when the point of interest appears to reach a maximum distance from the apparent axis of rotation on the display screen. This determines the angular position coordinate $\theta$ of the point of interest. It should be noted that a particular angular view or frame in the set of two-dimensional views or frames is associated with this point. This is because, assuming, for example, that the point of interest lies in a plane behind the plane which is parallel to the camera face and which includes the axis of rotation of the camera or the body, and further assuming that the display means 9 is illustrating a two-dimensional view which is at the chosen zero reference angle, the point of interest will appear on the display at a particular point along the x-axis which will appear to be closer to the axis of rotation than when the display means 9 is showing the particular view of the object at the angle which actually includes the point of interest. This is illustrated in FIG. 3 which shows the four frames of FIG. 2b. Although FIGS. 2b and 3 are simplified in that the successive views are only 90° apart from one another, whereas in actual practice, the angular views will be usually a few degrees apart, e.g., 3°–6°, these figures nevertheless illustrate the principles of the present invention. Thus, FIG. 4 illustrates the view of the point of interest for views taken in succession at 0°, 90°, 180°, and 270°. The point of interest "A" at each of these angles is marked on display 9 in FIG. 4, and appear to move in harmonic motion between the two end points. The frame associated with the end points are taken to represent the angular position of the point of interest "A" in relation to a chosen zero reference angle, as described above. This is because the angle through which the frames associated with display means or cine 9 must move for this maximum distance to occur determines the angular position $\theta$ for the point of interest. The cine is preferably provided with scroll back and forth throughout the images to enable the user to hit the exact frame at which the maximum distance occurs.

Figure 5:
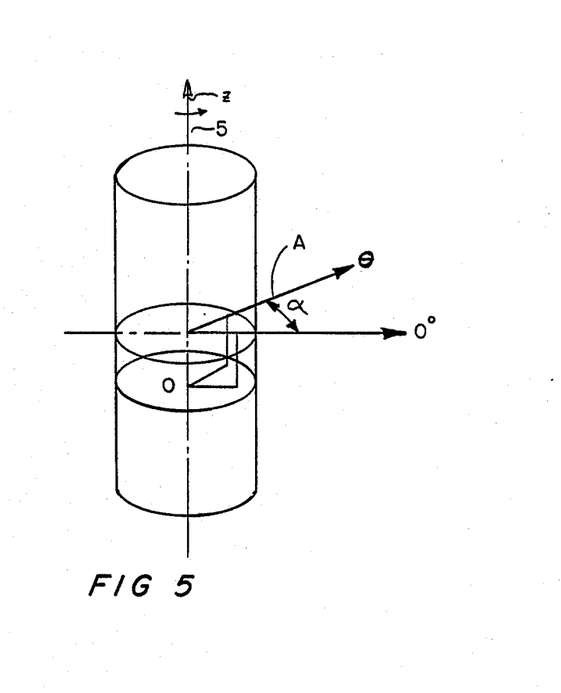
FIG. 5 illustrates the technique of stopping the display at a particular angular view after the displayed image has "rotated" through an angle such that the point of interest is at a maximum distance from the apparent axis of rotation of the displayed image.

Next, with display means 9 stopped or frozen at the frame which shows the point of interest at the above-described maximum distance from the apparent axis of rotation, a position indicating means associated with the display means is moved on the screen until it overlies the point of interest. This determines two additional coordinates; i.e., $r_0$, the radial distance from a chosen zero radius point, and $Z_0$, the height above a chosen zero height. This technique determines $r_0$ because at this maximum distance point it is known that the point of interest is in a plane which is parallel to the face of imaging means 3 and which includes the axis of rotation. Moreover, because, as described above, perpendicular, parallel-hole collimators are utilized with the gamma camera embodiment, $Z_0$ is easily obtained.

Finally, the operation of display means 9 is resumed, with the position indicating means "rotating" with the body. A computer can be used to calculate the projected location of the position indicating means for each view associated with each angle $\theta$ taken by the camera, i.e., for each frame. Each view has a given $\theta$ therefore a set of position indicating means "projections" are created at the point ($\theta$, $r(\theta)$, $Z_0$) which are superimposed on the views. This resumption of motion of the cine, i.e., rotation of the views having the superimposed position indicating means, is necessary to assure the user that the correct location has indeed been pinpointed.

In the technique in which the cursor is aligned with the point of interest during operation of display means 9, the position indicating means can be moved in three-dimensions. Where display means 9 is a cine and the position indicating means is a cursor, the cursor can be moved in three-dimensions by using a joystick and a punch key associated with the cine. For example, the joy stick controls $Z_0$ and $r(\theta)$ while the punch key controls $\theta$. Alternatively, the up/down motion of the joystick can determine $Z_0$ while the punch key determines whether the left/right motion of the joystick controls $\theta_0$ or $Z_0$. Again, a computer is used to calculate the projected location for a given position of the position indicating means or cursor for each view, even as the position indicating means is being moved. Thus, at each moment, an entire set of cursor projections is defined so that the user perceives position indicating means "rotating" in unison with the body, and always at the same rate as the body. By aligning the indicating means with the point of interest while the body and the position indicating means "rotate", an exact location, i.e., ($\theta_0$ $r(\theta_0)$ and $Z_0$) for the point of interest is immediately available. This method is advantageous because $\theta_0$ can be found even if no image was obtained at exactly that angle.

According to the present invention, the three-dimensional position of a point of interest in a body can be non-reconstructively determined by generating a set of two-dimensional views of the body from successive angular increments about a given axis by measuring the amount of radiation emitted by the body after injecting the body with a substance labeled with a radioactive tracer. The two-dimensional views so generated are successively displayed on a display means, and the three-dimensional coordinates associated with the location of the point of interest within the body are established. The projected location of the point of interest in each view in the set of two-dimensional views is calculated, and these projected locations are displayed for each view as each view is displayed on the display means.

Also according to the present invention, a method of determining the position of a point of interest in a body is provided by generating a set of two-dimensional views of the body from successive angular increments about a given axis, and determining the two-dimensional view within this set which is closest to the point of interest. This closest two-dimensional view is marked at a point which is closest to the point of interest, and the two-dimensional view with this marking is displayed. The two-dimensional view which is closest to the point of interest can be determined by successively displaying the two-dimensional views on a display means and stopping the display means at a particular angular view at which the point of interest is approximately at a maximum distance from an apparent axis of rotation of the two-dimensional views being successively displayed on the display means. Alternatively, the closest two-dimensional view is marked at a point which is closest to the point of interest by moving a position indicating means associated with the display means to superimpose the position indicating means over the displayed point of interest while the two-dimensional views are being successively displayed on the display means, and simultaneously with moving the position indicating means, the projected location for the position indicating means in each view in the set of two-dimensional views is calculated and displayed such that for each point to which the position indicating means is moved, the position indicating means appears to rotate about the apparent axis of rotation of the two-dimensional views on the display means in synchronism with the apparent rotation of the two-dimensional views.

Reference points can be set for establishing the zero reference points for the coordinate system for defining the spatial location of the point of interest within the body at internal points, such as the tip of the sternum, or external points, such as a radioactive marker. While the preferred method of obtaining the initial coordinates refers to a spherical coordinate system as described above, the location of the point of interest can be translated from these spherical coordinates to relative Cartesian coordinates using known mathematical algorithms.

If it is also desired to reconstruct a composite image using the set of successive angular views, a further advantage of the present invention is that, after reconstruction, a mark, for example a cross or arrow, can be placed on the section with Z nearest to $Z_0$, at the coordinates ($\theta_0$, $r_0$). This will, for example, facilitate for a physician the task of recognizing organs he saw on the "rotating" display means or cine.

From the foregoing description, one skilled in the art can easily ascertain the essential characteristics of the present invention and, without departing from the spirit and scope thereof, can make various changes and modifications of the invention to adapt it to various usages and conditions.

I claim:

1. An apparatus for determining the three-dimensional position of a point of interest in a body, the apparatus comprising:
    (a) imaging means for recording a set of two-dimensional views of the body from successive azimuthal angles about a given axis;
    (b) storage means having frames for storing respective views of the body;
    (c) display means for successively and repetitively displaying the contents of said frames whereby the display shows the body rotating about said axis; and
    (d) means for establishing a cursor in the display such that the cursor appears to move with but not relative to the point of interest.

2. An apparatus for non-reconstructively determining the position of a point of interest in a body, comprising:
    (a) imaging means for recording a set of two-dimensional views of the body from successive azimuthal angular increments about a given axis;
    (b) display means for successively and repetitively displaying said two-dimensional views;
    (c) position indicating means for selectively marking an elemental area on a display screen associated with said display means;
    (d) processor means for calculating the projected location of a marked elemental area for each view in said set of two-dimensional views of the body; and
    (e) a control circuit which cooperates with said display means to display the projected location of said marked pixel for each view in said set of two-dimensional views of the body simultaneously with the successive display of said two-dimensional views, such that said marked elemental area appears to rotate in syncronism with said successively displayed two dimensional views on said display screen.

3. The apparatus as recited in claim 2 wherein said position indicating means comprises a cursor.

4. The apparatus as recited in claim 2 further comprising first memory means for storing data representing said set of two-dimensional views of the body.

5. The apparatus as recited in claim 2 further comprising second memory means for storing data representing said projected locations of said marked pixel.

6. A method of non-reconstructively determining the three-dimensional position of a point of interest in a body comprising:
    (a) generating a set of two-dimensional views of the body from successive angular increments about a given axis by measuring the amount of radiation emitted by the body after injecting the body with a substance labeled with a radioactive tracer:
    (b) successively displaying said two-dimensional views on a display means;
    (c) marking the position of said point of interest in at least one said view while said at least one view is being displayed on said display means;
    (d) calculating the projected location of said marked position in said at least one view for each remaining view in said set of two-dimensional views; and
    (e) displaying said projected locations for each view as said each view is displayed on said display means.

7. The method as recited in claim 6 further comprising stopping said display means at a particular angular view at which said point of interest is approximately at a maximum distance from an apparent axis of rotation of said two-dimensional views being successively displayed on said display means.

8. The method as recited in claim 7 further comprising determining the angular position within said body which corresponds to the particular view at which said display is stopped.

9. The method as recited in claim 8 wherein said corresponding angular position is determined by ascertaining the angular position of said particular view at which said display is stopped with respect to a reference angle.

10. The method as recited in claim 8 further comprising determining the position within said body which corresponds to the radial and height positions of said point of interest in said particular view at which said display is stopped.

11. The method as recited in claim 10 further comprising verifying said determined positions by marking said point of interest in said particular view at which said display is stopped, calculating the projected location of said marked position in said particular view for each remaining view, and successively displaying said two-dimensional views simultaneously with said projected locations of said marked position to verify that said point of interest and said marked position are superimposed in each view in said set of two-dimensional views.

12. A method of non-reconstructively determining the three-dimensional position of a point of interest in a body comprising:
 (a) generating a set of two-dimensional views of the body from successive angular increments about a given axis by measuring the amount of radiation emitted by the body after injecting the body with a substance labelled with a radioactive tracer;
 (b) successively displaying said two-dimensional views on a display means;
 (c) establishing three-dimensional co-ordinates associated with the location of said point of interest within said body;
 (d) calculating the projected location of said point of interest in each view in said set of two-dimensional views; and
 (e) displaying said projected locations for each view as said each view is displayed on said display means.

13. The method as recited in claim 12 further comprising moving a position indicating means associated with said display means to superimpose said position indicating means over said displayed point of interest while said two-dimensional views are being successively displayed on said display means, and simultaneously with moving said position indicating means, calculating and displaying the projected location for said position indicating means in each view in said set of two-dimensional views such that for each point to which said position indicating means is moved, said position indicating means appears to rotate about the apparent axis of rotation of said two-dimensional views on said display means in synchronism with the apparent rotation of said two-dimensional views.

14. The method as recited in claim 13 wherein said position indicating means is a cursor.

15. The method as recited in claim 13 further comprising determining the location within said body of said point of interest which corresponds to the position of said position indicating means at which said position indicating means is superimposed over said displayed point of interest for each view in said set of two-dimensional views.

16. The method as recited in claim 12 wherein said three-dimensional coordinates associated with the location of said point of interest within said body are established by marking the position of said point of interest in at least one view by superimposing a position indicating means associated with said display means over said point of interest.

17. The method as recited in claim 16 wherein said position indicating means is a cursor.

18. A method of determining the position of a point of interest in a body comprising:
 (a) generating a set of two-dimensional views of the body from successive angular increments about a given axis;
 (b) determining the two-dimensional view within said set which is closest to said point of interest;
 (c) marking said closest two-dimensional view at a point which is closest to said point of interest; and
 (d) displaying said two-dimensional view with said marking.

19. The method as recited in claim 18 wherein said two-dimensional view which is closest to said point of interest is determined by successively displaying said two-dimensional views on a display means and stopping said display means at a particular angular view at which said point of interest is approximately at a maximum distance from an apparent axis of rotation of said two-dimensional views being successively displayed on said display means.

20. The method as recited in claim 19 further comprising determining the angular position within said body which corresponds to the particular view at which said display is stopped.

21. The method as recited in claim 20 wherein said corresponding angular position is determined by ascertaining the angular position of said particular view at which said display is stopped with respect to a reference angle.

22. The method as recited in claim 20 further comprising determining the position within said body which corresponds to the radial and height positions of said point of interest in said particular view at which said display is stopped.

23. The method as recited in claim 22 further comprising verifying said determined positions by marking said particular view at which said display is stopped at a point which is closest to said point of interest, calculating the projected location of said marked position in said particular view for each remaining view, and successively displaying said two-dimensional views simultaneously with said projected locations of said marked position to verify that said point of interest and said marked position are superimposed in each view of said set of two-dimensional views.

24. The method as recited in claim 18 wherein said closest two-dimensional view is marked at a point which is closest to said point of interest by moving a position indicating means associated with said display means to superimpose said position indicating means over said displayed point of interest while said two-dimensional views are being successively displayed on said display means, and simultaneously with moving said position indicating means, calculating and displaying the projected location for said position indicating means in each view in said set of two-dimensional views such that for each point to which said position indicating means is moved, said position indicating means appears to rotate about the apparent axis of rotation of said two-dimensional views on said display means in synchronism with the apparent rotation of said two-dimensional views.

25. The method as recited in claim 24 wherein said position indicating means is a cursor.

26. The method as recited in claim 24 further comprising determining the location within said body of said point of interest which corresponds to the position of said position indicating means at which said position indicating means is superimposed over said displayed point of interest for each view in said set of two-dimensional views.

27. The method as recited in claim 18 wherein said closest two-dimensional view is marked at a point which is closest to said point of interest by superimposing a position indicating means associated with said display means over said point of interest.

28. The method as recited in claim 27 wherein said position indicating means is a cursor.

29. One method of determining the three dimensional position of a point of interest in a body, said method comprising the steps of:
 (a) generating a set of two dimensional interior views of the body from incremental angular positions about a given axis, (b) reconstructing a plurality of transverse planes through said set of two dimensional views,
(c) marking the transverse plane nearest the point of interest at a point nearest the point of interest, and
(d) displaying the transverse plane with the marking thereon.

30. An apparatus for determining the three dimensional position of a point of interest in a body, the apparatus comprising:

(a) means for generating a set of two dimensional interior views of the body from incremental angular positions about a given axis,
(b) means for reconstructing transverse planes through said body from said sets of two dimensional views,
(c) means for marking the transverse plane nearest the point of interest at a point nearest the point of interest, and
(d) means for displaying the transverse plane with the marking thereon.

* * * * *